United States Patent
Regere et al.

(10) Patent No.: US 8,758,011 B2
(45) Date of Patent: Jun. 24, 2014

(54) DENTAL TREATMENT APPLIANCE WITH AUTOMATIC TIP RECOGNITION

(75) Inventors: Pascal Regere, Blanquefort (FR); Francis Dieras, Bordeaux (FR)

(73) Assignee: Societe pour la Conceptions des Applications des Techniques Electroniques (SATELEC), Merignac Cedex (FR)

( * ) Notice: Subject to any disclaimer, the term of this patent is extended or adjusted under 35 U.S.C. 154(b) by 1060 days.

(21) Appl. No.: 11/883,622

(22) PCT Filed: Feb. 1, 2006

(86) PCT No.: PCT/FR2006/050085
§ 371 (c)(1),
(2), (4) Date: Apr. 10, 2008

(87) PCT Pub. No.: WO2006/082340
PCT Pub. Date: Aug. 10, 2006

(65) Prior Publication Data
US 2008/0293008 A1    Nov. 27, 2008

(30) Foreign Application Priority Data
Feb. 2, 2005  (FR) .................................. 05 01050

(51) Int. Cl.
*A61C 17/20* (2006.01)
*A61C 1/07* (2006.01)

(52) U.S. Cl.
USPC ....................................................... 433/119

(58) Field of Classification Search
USPC ............... 433/27, 98, 99, 116, 118, 119, 143
See application file for complete search history.

(56) References Cited

U.S. PATENT DOCUMENTS

| | | | |
|---|---|---|---|
| 4,283,175 A | 8/1981 | Nash | |
| 4,705,038 A * | 11/1987 | Sjostrom et al. | 606/180 |
| 5,400,267 A * | 3/1995 | Denen et al. | 702/59 |
| 5,451,161 A * | 9/1995 | Sharp | 433/119 |
| 5,632,759 A * | 5/1997 | Rexroth | 606/180 |
| 5,769,791 A * | 6/1998 | Benaron et al. | 600/473 |
| 6,312,256 B1 | 11/2001 | Dieras et al. | |
| 6,503,081 B1 | 1/2003 | Feine | |
| 6,545,390 B1 * | 4/2003 | Hahn et al. | 310/317 |

(Continued)

FOREIGN PATENT DOCUMENTS

| | | |
|---|---|---|
| DE | 37 08 801 A1 | 9/1988 |
| DE | 197 33 501 A1 | 2/1999 |
| FR | 04 06630 | 12/2005 |
| WO | WO9905984 * | 2/1999 |

OTHER PUBLICATIONS

English language specification corresponding to WO 99/05984.*

*Primary Examiner* — Todd Manahan
*Assistant Examiner* — Michael R Ballinger
(74) *Attorney, Agent, or Firm* — Workman Nydegger (57) ABSTRACT

An ultrasound dental treatment appliance having a surgical handpiece (220) fitted with a transducer connected to an ultrasound generator (230), the handpiece being designed to receive ultrasound tips (210) that are mechanically coupled to the transducer and that operate in different ultrasound wave power and amplitude ranges. The dental treatment appliance includes elements (224, 225), e.g. optical elements, for automatically detecting the utilization power and amplitude range of the tip (210) mounted on the handpiece, and a processor for automatically setting the ultrasound generator to the detected power and amplitude range.

8 Claims, 7 Drawing Sheets

(56) References Cited

U.S. PATENT DOCUMENTS

| | | | |
|---|---|---|---|
| 6,666,860 B1 * | 12/2003 | Takahashi | 606/34 |
| 6,899,538 B2 * | 5/2005 | Matoba | 433/114 |
| 6,994,707 B2 * | 2/2006 | Ellman et al. | 606/42 |
| 2001/0029315 A1 * | 10/2001 | Sakurai et al. | 600/101 |
| 2003/0115694 A1 * | 6/2003 | Pace | 15/22.1 |
| 2003/0222535 A1 * | 12/2003 | Gofman et al. | 310/316.01 |
| 2004/0063064 A1 | 4/2004 | Feine | |
| 2004/0255409 A1 | 12/2004 | Hilscher et al. | |
| 2004/0267297 A1 * | 12/2004 | Malackowski | 606/167 |
| 2007/0254262 A1 | 11/2007 | Doussin et al. | |

\* cited by examiner

DENTAL TREATMENT APPLIANCE WITH AUTOMATIC TIP RECOGNITION

BACKGROUND OF THE INVENTION

The present invention relates to dental treatment appliances, and more particularly to ultrasound appliances, such as scaling appliances, surfacing appliances (for eliminating biofilms), or cutting appliances (cavities or preparations for a prosthesis), all comprising instruments that vibrate at ultrasound frequencies.

Figure 1:
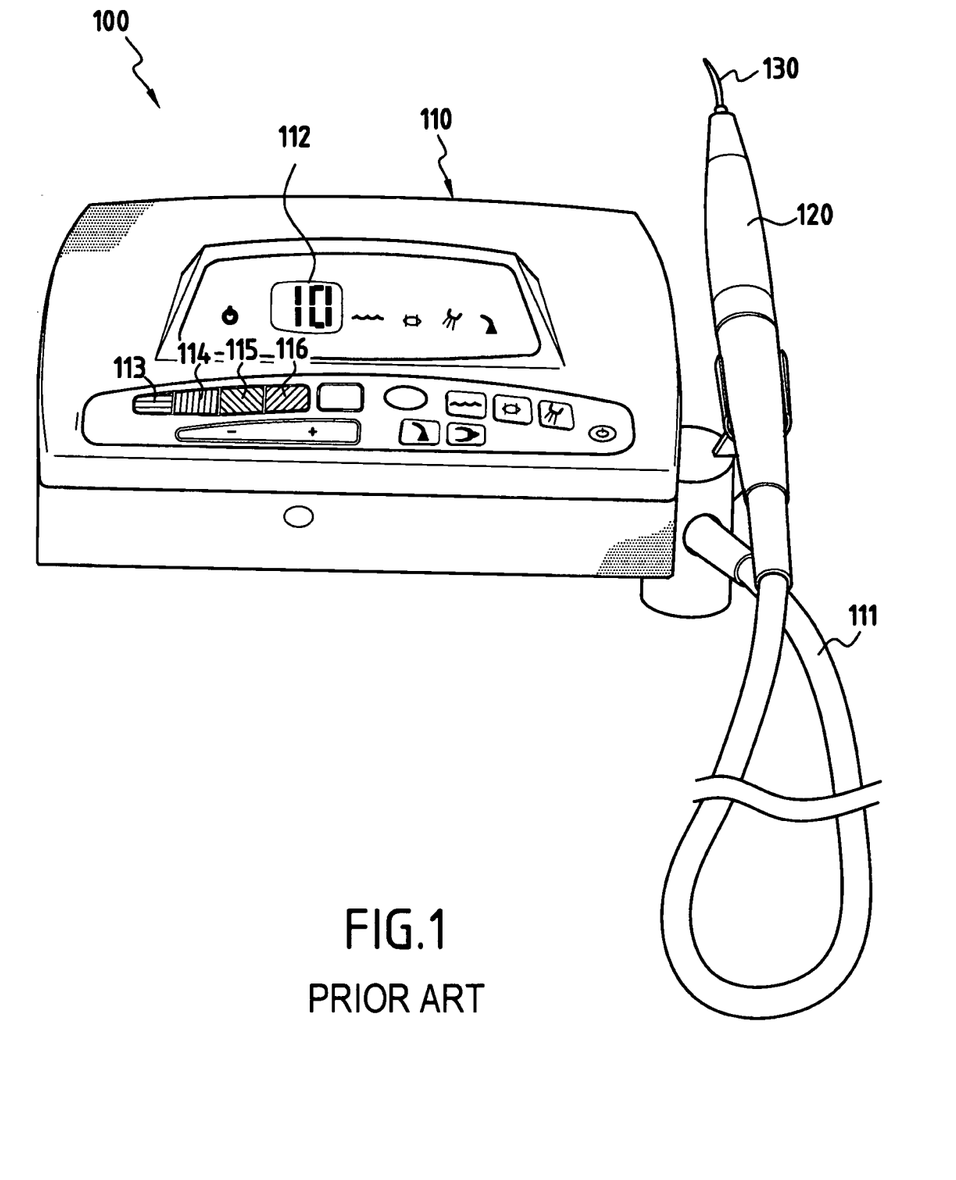
FIG. 1 is a diagrammatic view of an ultrasound dental surgery appliance.

FIG. 1 shows an ultrasound treatment appliance 100 that comprises an ultrasound generator 110 connected to a handpiece 120 via a cord 111. A sonotrode or ultrasound tip 130 is mounted at the end of the handpiece 120. In well-known manner, the handpiece 120 includes a transducer (not shown) e.g. made of piezoelectric material, and coupled mechanically to the tip 130 in such a manner as to transmit vibratory waves thereto at an amplitude that is determined as a function of the power delivered by the ultrasound generator 110.

The tip is an interchangeable part that presents a wide variety of shapes depending on the treatment for which it is intended. Examples of such tips are described in particular in U.S. Pat. Nos. 6,312,256 and 4,283,175. The amplitude or the power of the ultrasound waves transmitted by the generator also depends on the type of treatment that is to be applied. For example, for periodontal debridement, the required power/amplitude is much less than that required for removing scale. In addition, the type of tip used may differ as a function of the treatment to be performed. Consequently, for each type of dental treatment, there exist one or more families of tips that are for operating with ultrasound waves in respective determined power and amplitude ranges.

Consequently, dental treatment appliances include an ultrasound generator of power that can be adjusted as a function of the treatment being performed and/or of the tip in use. In order to make such appliances easier for practitioners to use, ultrasound generators are fitted with buttons or keys 113 to 116, for example, that make it possible automatically to select a power range that is appropriate for the treatment. These keys are identified by a color code or the equivalent enabling the practitioner to select the appropriate power range, and once selected, the range can be specified on a screen 112.

Nevertheless, as explained above, specific tips are also used for each treatment that are themselves intended to operate in one of the power ranges preadjusted on the appliance. Consequently, the practitioner must also verify that the tip placed on the handpiece is well adapted to the selected power range, or conversely must select the power range that corresponds to the tip mounted on the handpiece.

For this purpose, one of the known solutions consists in packaging each tip on a distinctive support element. The support element carries marking that matches that of the power range selection keys. For example, if the keys are identified by a color code, each support presents a color code corresponding to that of the key used for selecting the best power range for the tip placed on the support.

Another solution consists in marking the tip directly with a color code or the like enabling the practitioner to identify the power range for using the tip. This type of tip marking is described in French patent document FR 04/06630.

Nevertheless, whatever the identification technique used, selecting the power range on the ultrasound generator requires intervention on the part of the practitioner, thereby complicating the use of the dental treatment appliance for the practitioner, and not eliminating the risk that the wrong power range might be selected on the generator.

U.S. Pat. No. 6,503,081 describes an ultrasound appliance comprising a handpiece fitted with a magnetostrictive element connected to an ultrasound generator. The ultrasound generator has processor means programmed to apply a series of signals of varying frequency to the magnetostrictive element of the handpiece carrying a tip and to measure the consumption of the magnetostrictive element in order to detect the frequency that corresponds to the resonant frequency of the handpiece fitted with the tip. Thereafter the processor means adjust the generator to said detected resonant frequency. However, although that document discloses a solution for detecting and adjusting the ultrasound generator on the resonant frequency of the tip mounted on the handpiece, it does not enable the type of tip mounted on the handpiece to be identified. Without the tip being recognized specifically, it is not possible to adjust the generator on a power and amplitude range that is adapted to the type of tip mounted on the handpiece.

OBJECT AND SUMMARY OF THE INVENTION

An object of the present invention is to remedy the above-mentioned drawbacks and to propose a solution that avoids any intervention on the part of the practitioner, while nevertheless adjusting the power and amplitude range of the ultrasound generator to match the type of tip used.

This object is achieved by an ultrasound dental treatment appliance comprising at least one surgical handpiece fitted with a transducer connected to an ultrasound generator, said handpiece being designed to receive ultrasound tips that are mechanically coupled to the transducer and that operate in different ultrasound wave power and amplitude ranges, the appliance being characterized in that it includes means for automatically detecting the utilization power and amplitude range of the tip mounted on the handpiece, said range extending between a lower limit and an upper limit defining respective minimum and maximum utilization power and amplitude values for the detected tip, and processor means for automatically setting the ultrasound generator to the detected power and amplitude range.

Thus, the dental treatment appliance of the invention is capable of automatically recognizing the type of tip mounted on the handpiece and of responding thereto by adjusting its ultrasound generator to a power and amplitude range matching the type of tip that has been recognized. The type of tip is detected by reading (optically or by radio) an identity code or by analyzing the response signal of the handpiece transducer. Each identity code or response signal corresponds to its own power and amplitude range that is stored in the appliance, thereby enabling the processor means of said appliance to adjust the ultrasound generator automatically on the power and amplitude range that corresponds to the detected type of tip.

The practitioner no longer needs to take action in order to adjust the power and amplitude range in which the tip is to be used. Consequently, use of the appliance is simplified and any risk of error in selecting the power and amplitude range for the ultrasound waves delivered by the generator is eliminated. After recognizing the tip, the appliance of the invention sets itself automatically in a power and amplitude range defining a minimum power and amplitude value below which the tip does not operate effectively, and a maximum power and amplitude value above which the strength of the tip might suffer. This makes it possible for the practitioner to use the tip within a power and amplitude range that guarantees the tip is fed at a power and an amplitude that are always sufficient to enable the tip to be used effectively and never so great so as to run the risk of damaging it. The appliance of the invention thus provides the practitioner with increased safety and comfort in use.

In an embodiment of the invention, the appliance includes optical reader means for reading a code, such as a bar code, on the tip and corresponding to the type of tip, so as to identify the ultrasound power and amplitude range in which the tip is to operate.

In another embodiment of the invention, the appliance includes radio reader means, such as a radio frequency identification (RFID) reader, for reading a code stored in the tip and corresponding to the type of tip, so as to determine the ultrasound power and amplitude range in which the tip is to be operated.

In yet another embodiment of the dental treatment appliance of the invention, the appliance includes means for sending an electronic measurement signal to the transducer that is mechanically coupled to a tip, and means for measuring and analyzing the response signal of the transducer, said response signal including information corresponding to the type of the tip and suitable for determining the ultrasound power and amplitude range in which the tip is to operate.

The signal may be analyzed in terms of frequency. Under such circumstances, the appliance includes a wobulator for sending a measurement signal to the transducer at a determined frequency and processor means for analyzing the response signal from the transducer in such a manner as to determine at least one of the following parameters from the response signal: resonant frequency, phase, power, and impedance, with one or more of these parameters corresponding to the type of the tip and making it possible to determine the ultrasound wave power and amplitude range in which the tip coupled to the transducer is to be operated.

The response signal from the transducer may also be analyzed in the time domain. Under such circumstances, the appliance includes means for sending an impulse signal (e.g. a Dirac impulse) to the transducer and processor means for analyzing the response signal from the transducer in the time domain, said time-domain response signal (tip signature) corresponding to the type of tip mounted on the handpiece and making it possible to determine the ultrasound wave power and amplitude range in which the tip coupled to the transducer is to be operated.

The present invention also provides an ultrasound tip for mounting on a surgical handpiece of an ultrasound dental treatment appliance, characterized in that it includes means for automatically identifying the ultrasound wave power and amplitude range in which the tip is designed to operate, said range extending between a lower limit and an upper limit defining respective minimum and maximum power and amplitude values for use of the detected tip.

The tip may include a bar code written on its base or a transponder (RFID) enabling the ultrasound dental treatment appliance to recognize the type of the tip and to select automatically the ultrasound wave power and amplitude range in which the tip is to be operated.

BRIEF DESCRIPTION OF THE DRAWINGS

Other characteristics and advantages of the invention appear from the following description of particular embodiments of the invention given as non-limiting examples and with reference to the accompanying drawings, in which.

DETAILED DESCRIPTION OF EMBODIMENTS OF THE INVENTION

Figure 2:
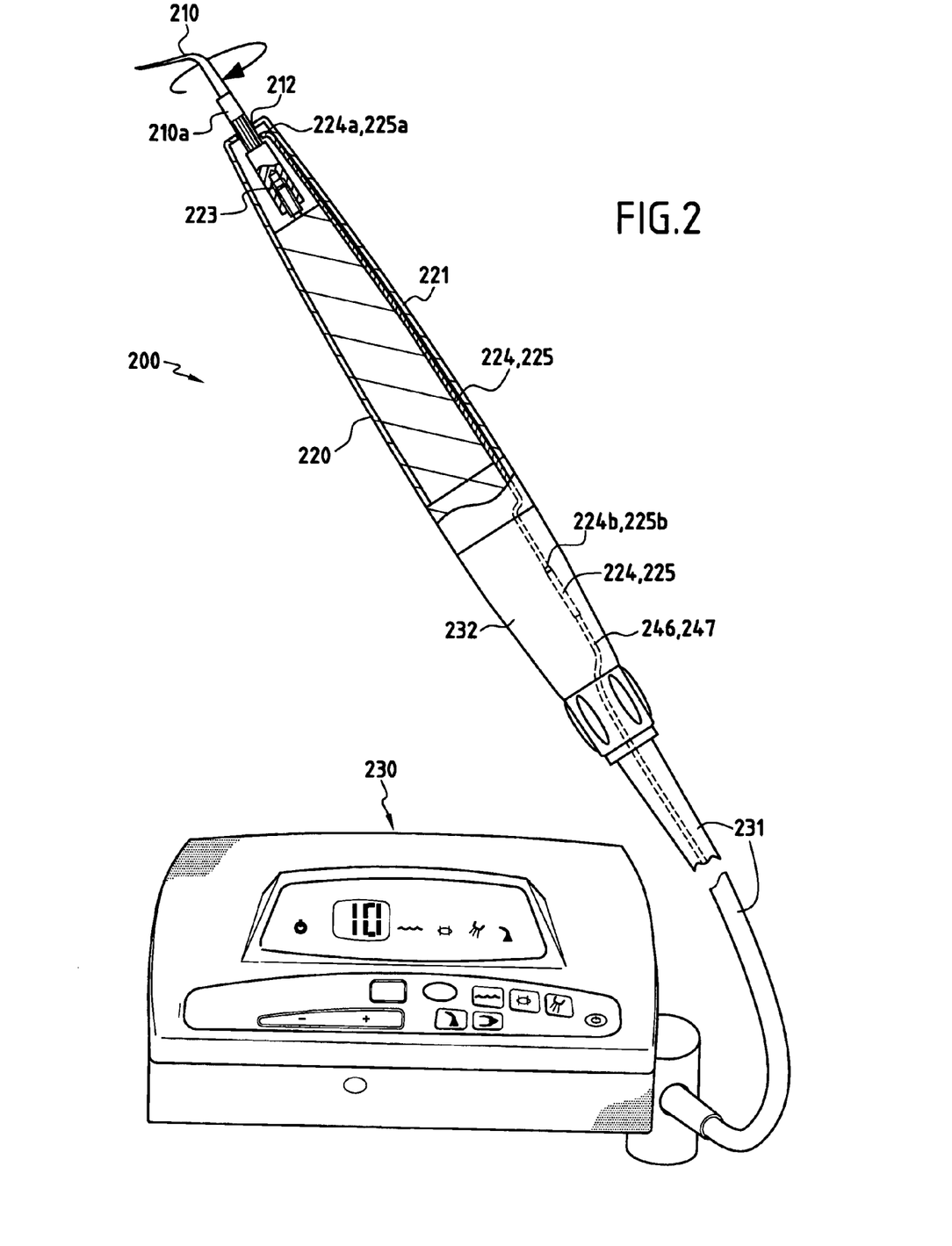
FIG. 2 is a diagrammatic view of an ultrasound dental surgery appliance constituting a first embodiment of the invention.

FIG. 2 shows an ultrasound dental treatment appliance 200 constituting a first embodiment of the invention. The appliance 200 is constituted by a handpiece 220 provided with a tip 210 and connected to an ultrasound generator 230 by means of a cord 231.

The ultrasound appliance in this embodiment includes means for optically detecting the type of tip for determining the power and amplitude range in which the tip is to be used. For this purpose, and as shown in FIG. 2, the appliance uses a tip 210 that carries a bar code 212 placed around its base 210a. In conventional manner, the tip is mechanically coupled in rigid manner to the transducer (not shown) of a handpiece 220 by being screwed onto an element 223 secured to the transducer (not shown) of the handpiece 220. Two optical fibers 224 and 225 are placed side by side in the body 221 of the handpiece. The fibers 224 and 225 are molded in the body 221, for example. The respective ends 224a and 225a of the optical fibers 224 and 225 open out from the body 221 level with the base 210a of the tip 210 in a position that is perpendicular to the surface of the base so that the bar code 212 of the tip is caused to travel past these ends while the tip is being screwed onto the handpiece.

Figure 3A:
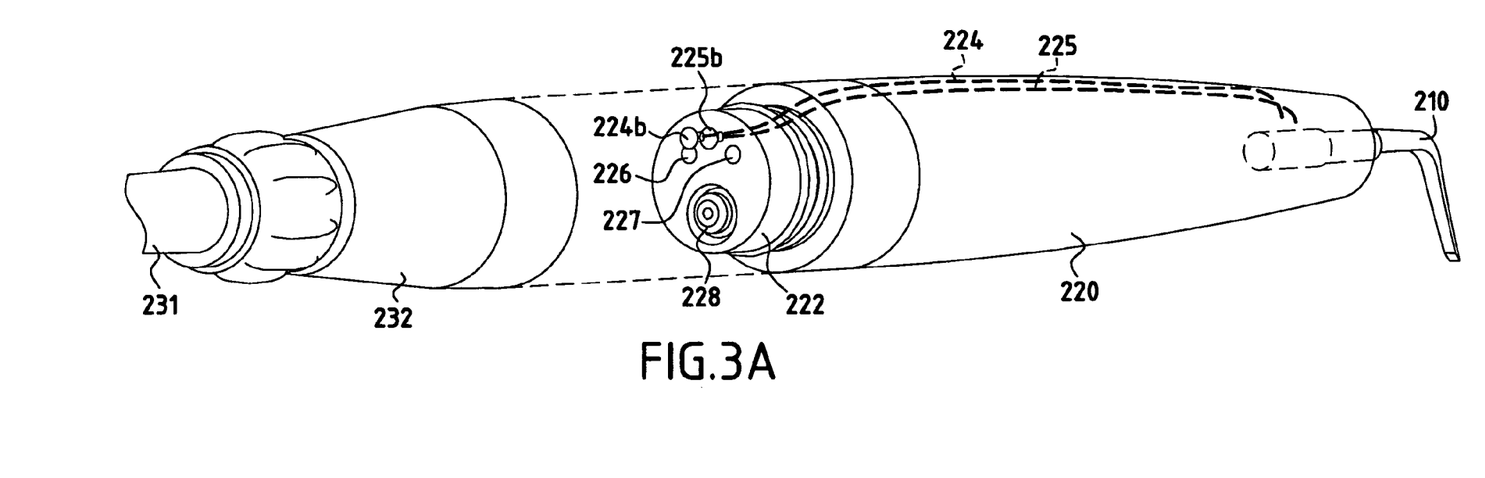
FIGS. 3A and 3B are diagrammatic perspective views showing the handpiece and the cord connector of the FIG. 2 ultrasound generator.
Figure 3B:
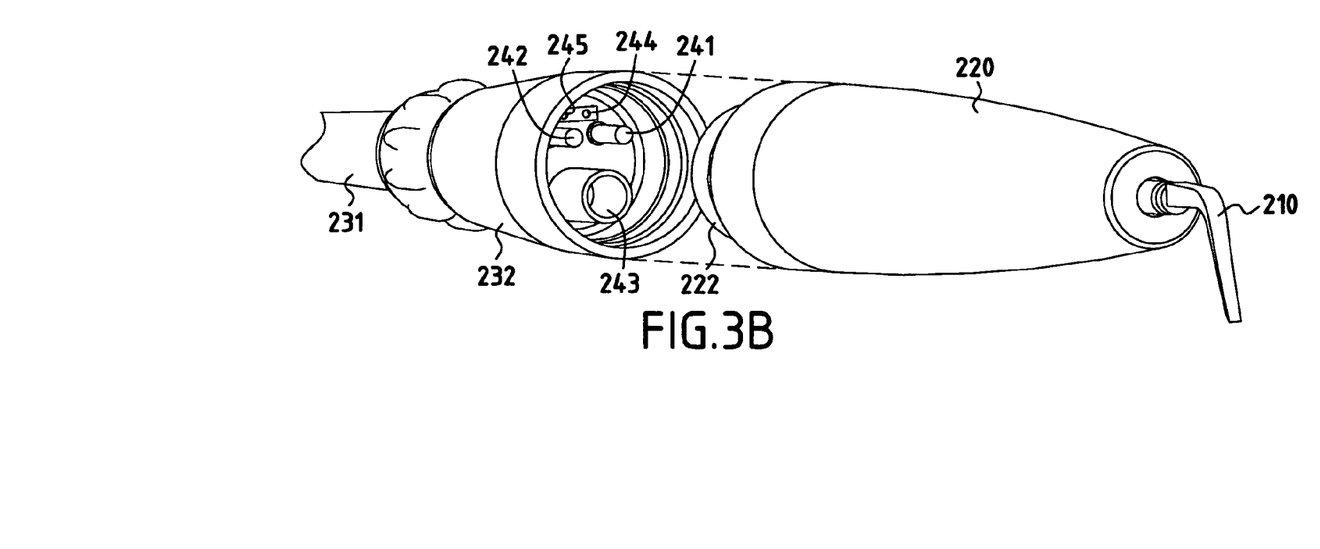

As shown in FIG. 3A, the other ends 224b and 225b of the fibers 224 and 225 open out in the bottom of the connector 222 of the handpiece 220 close to two female sockets 226 and 227 and an irrigation duct 228. As shown in FIG. 3B, the ends 224b and 225b of the fibers 224 and 225, the female sockets 226 and 227, and the duct 228 co-operate respectively with a light-emitting diode (LED) 244 or any other light-emitting component, with a photodetector (diode, transistor, etc.) 245, with two male plugs 241 and 242, and with a duct 243, all of these elements being placed inside a connector 232 and connected to one end of the cord 231, and in which the connector 222 of the handpiece engages.

The transducer of the handpiece is connected to the ultrasound generator 230 by engaging the plugs 241 and 242 respectively in the sockets 226 and 227. The irrigation duct 228 is fed with liquid by the duct 243. The operation of these elements is well known and is therefore not described in greater detail.

The LED 244 is connected to the ultrasound generator 230 by a conductor 246 housed in the cord 231, and the photodetector 245 is connected to the ultrasound generator 230 by a conductor 247 housed in the cord 231 (FIG. 2). These two elements are preferably placed in the connector 232 of the cord 231 so as to protect them from the autoclave cycles to which the handpiece is subjected. Only the optical fibers 224 and 225 need to be made of a material that can withstand the moist high-temperature conditions that are to be found in autoclaves.

Figure 4:
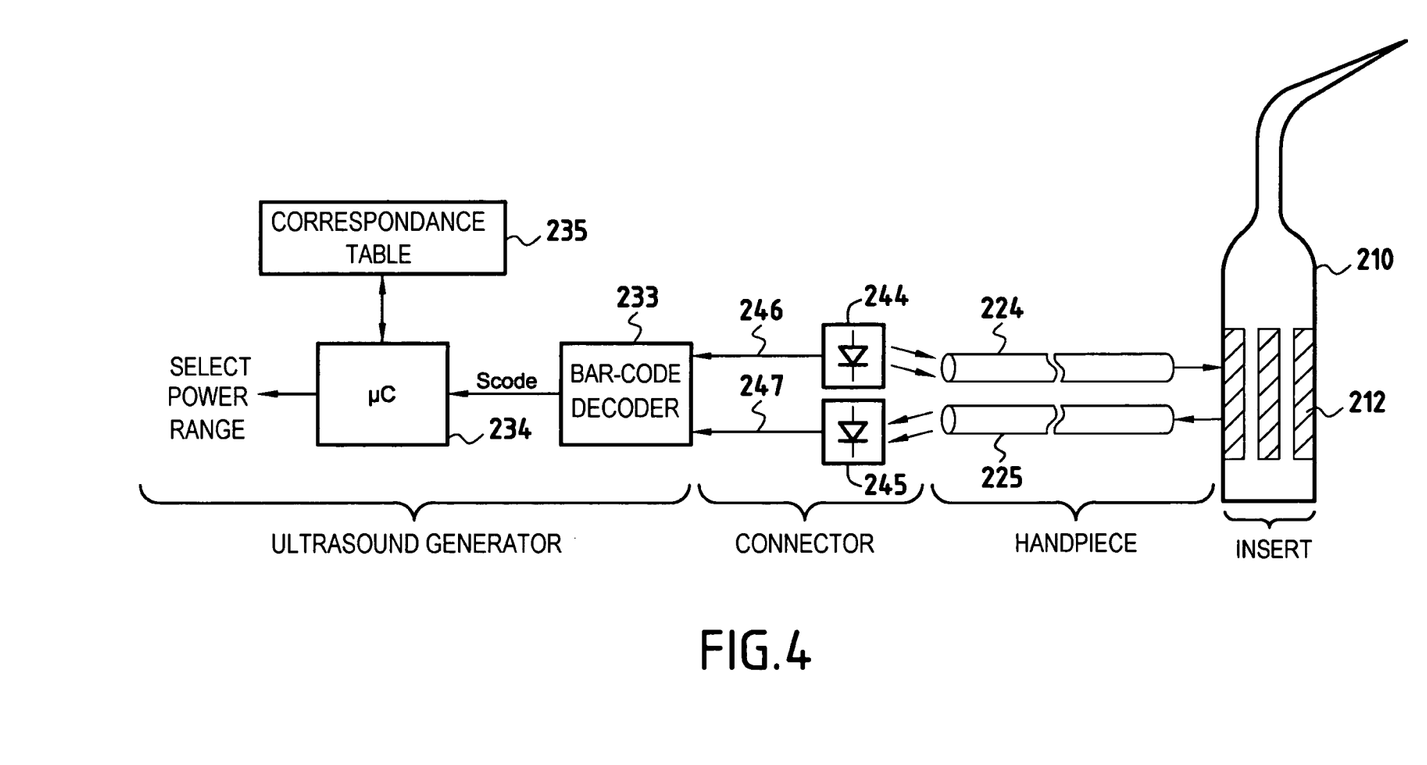
FIG. 4 is a block diagram of the FIG. 2 appliance.

FIG. 4 is a diagram showing the elements involved while optically recognizing a tip and automatically selecting the power range in this first embodiment. The ultrasound generator 230 includes a bar code decoder 233 that operates in well known manner. The decoder transmits an emission signal to the LED 244 via the conductor 246. The diode 244 then emits a modulated or continuous light signal which propagates along the optical fiber 224 to illuminate at its outlet the bar code 212 written on the base of the tip. The reflected light is conveyed to the photodetector 245 by the fiber 225. The photodetector 245 converts the light signal it receives into an electrical signal and transmits it to the decoder 233 via the conductor 247.

In application of the known principle of a bar code, the intensity of the light reflected by the tip, and consequently of the signal transmitted by the photodetector, is a function of the zone of the tip that is illuminated. More precisely, this signal takes a minimum value when a black bar faces the fiber 225 and takes a maximum value in the absence of such a bar, with the tip then presenting (between two bars) a highly reflective bright zone. Thus, the signal received while screwing the tip 210 onto the handpiece 220 comprises a burst of pulses corresponding to the coding written on the tip.

Figure 5:
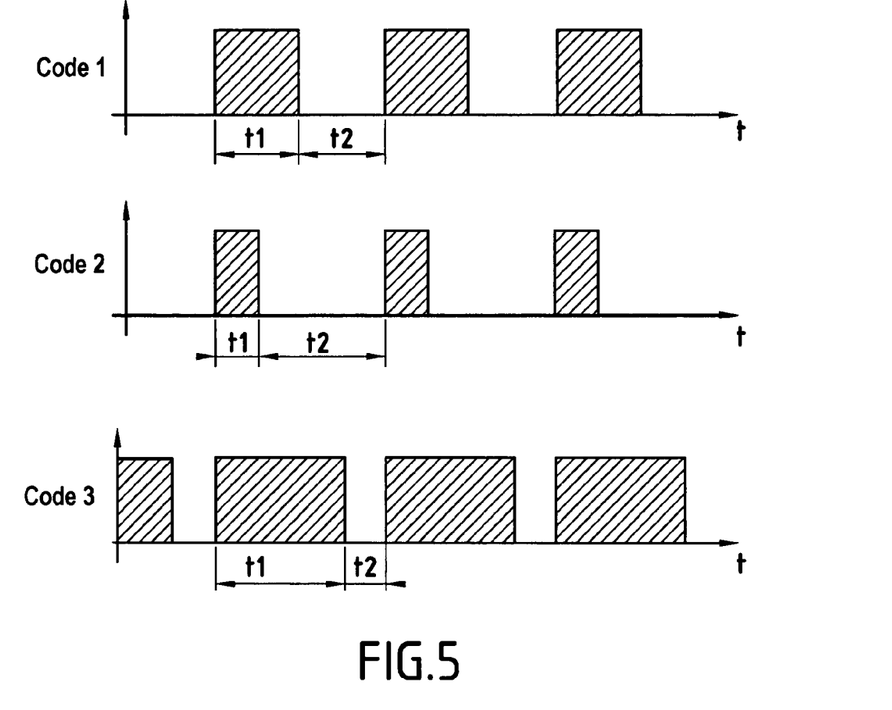
FIG. 5 shows examples of coding that can be written on the tip used in the first embodiment of the appliance of the invention.

The time measured between pulses and the widths (i.e. the durations) of these pulses enable the decoder 233 to deduce the code that is written on the tip. Nevertheless, the speed of screw tightening can vary from one user to another, or can vary over time with a single user. In order to avoid the code being read erroneously, the decoder 233 preferably decodes the information on the basis of the ratio t1/t2 which corresponds to the ratio between the duration t1 of each pulse and the duration t2 between two successive pulses, which ratio remains constant regardless of the speed with which the tip is tightened. Examples of codes using such a ratio are given in FIG. 5.

Once the information written on the tip has been decoded, the decoder 232 forwards the information to the processor means 234 (e.g. a microcontroller) in the form of an Scode signal which may correspond, for example, to ASCII characters. The processor means 234 are specifically programmed to select the utilization power range of the ultrasound generator that corresponds to the identified tip, e.g. by interrogating a look-up table 235 in which utilization power ranges are recorded for each type of tip.

Figure 6:
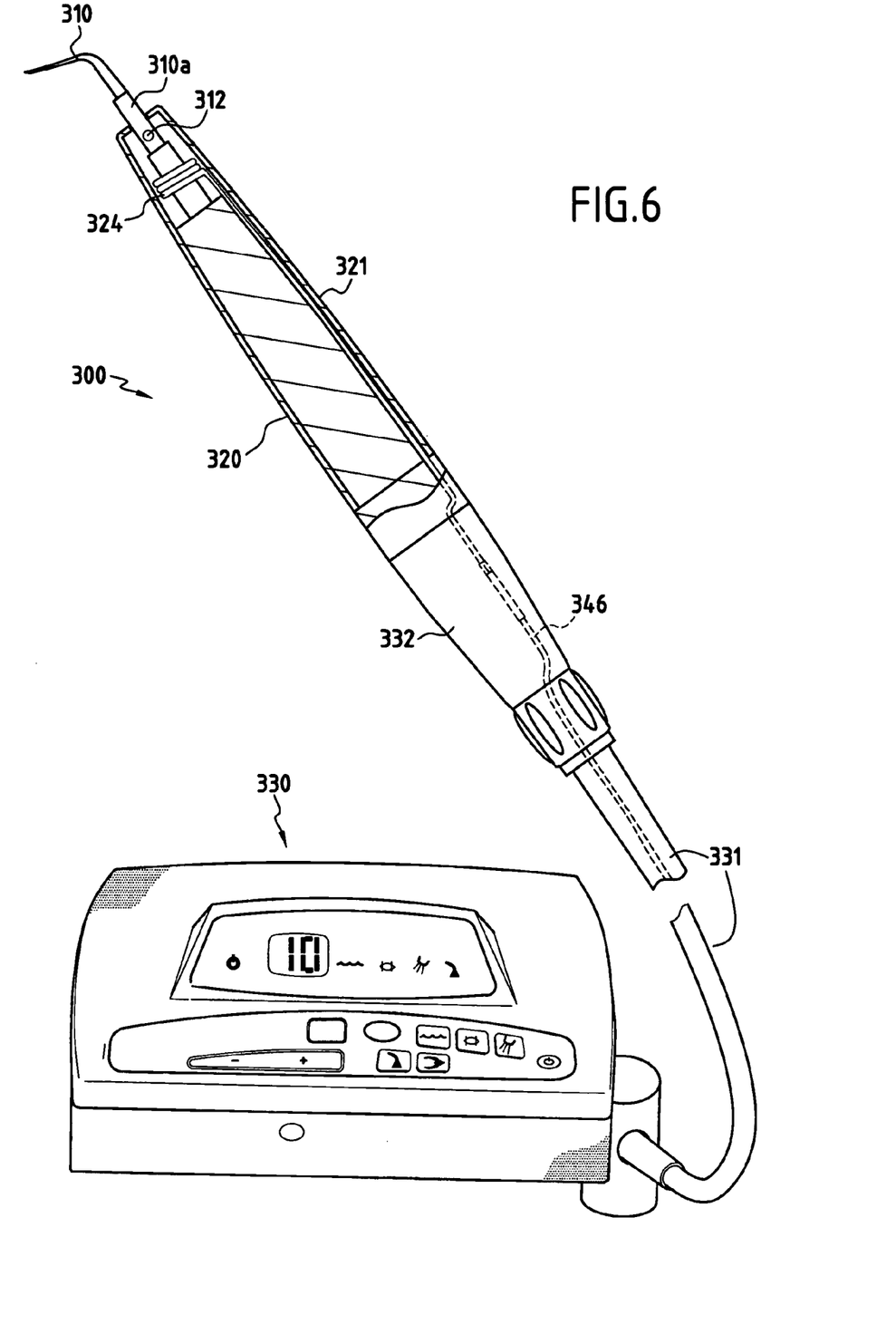
FIG. 6 is a diagrammatic view of an ultrasound dental surgery appliance constituting a second embodiment of the invention.

FIG. 6 shows an ultrasound treatment appliance 300 constituting a second embodiment of the invention and constituted by a handpiece 320 provided with a tip 310 and connected to an ultrasound generator 330 by means of a cord 331.

In this embodiment, the ultrasound appliance detects the power and amplitude range in which the tip is to be used by a radio frequency (RF) technique. For this purpose, and as shown in FIG. 6, the appliance uses a tip 310 which includes in its base 310a a transponder 312. The transponder 312 can be a miniature component using RFID technology. In well-known manner, this type of component is a passive circuit including an inductance-capacitance (LC) type resonator (antenna) suitable for picking up an electromagnetic field at a given frequency in order to power the component. This electromagnetic field is generated by a solenoid antenna 324 disposed in the body 321 of the handpiece 320 (e.g. by being molded therein).

Once it is powered, the circuit responds by delivering a radio signal containing a preprogrammed code. This code generates frequency modulation by fluctuating the capacitance of the LC resonator, thereby displacing its resonant frequency about the carrier frequency. The solenoid appliance 324 is connected to a capacitor (not shown) to form an LC type transceiver circuit which detects this frequency variation by fluctuations in the energy it absorbs. This fluctuation signal is then forwarded to the processor means (e.g. a microcontroller) of the ultrasound generator 330 via a conductor 346 housed in the cord 331. The processor means are programmed to convert the fluctuations of the received signal into binary data and to compare the data with that recorded in a correspondence table where the utilization power and amplitude ranges for each type of tip are stored as in the above-described appliance constituting the first embodiment. Once the type of tip has been recognized, the processor means set the ultrasound generator to the power an amplitude range that matches the tip mounted on the handpiece. As described above for recognition by bar code, the processor means of the ultrasound generator are programmed specifically to set the generator on the utilization power and amplitude range that corresponds to the identified tip, e.g. by interrogating a look-up table in which the utilization power ranges are recorded for each type of tip.

Figures 7, 9:
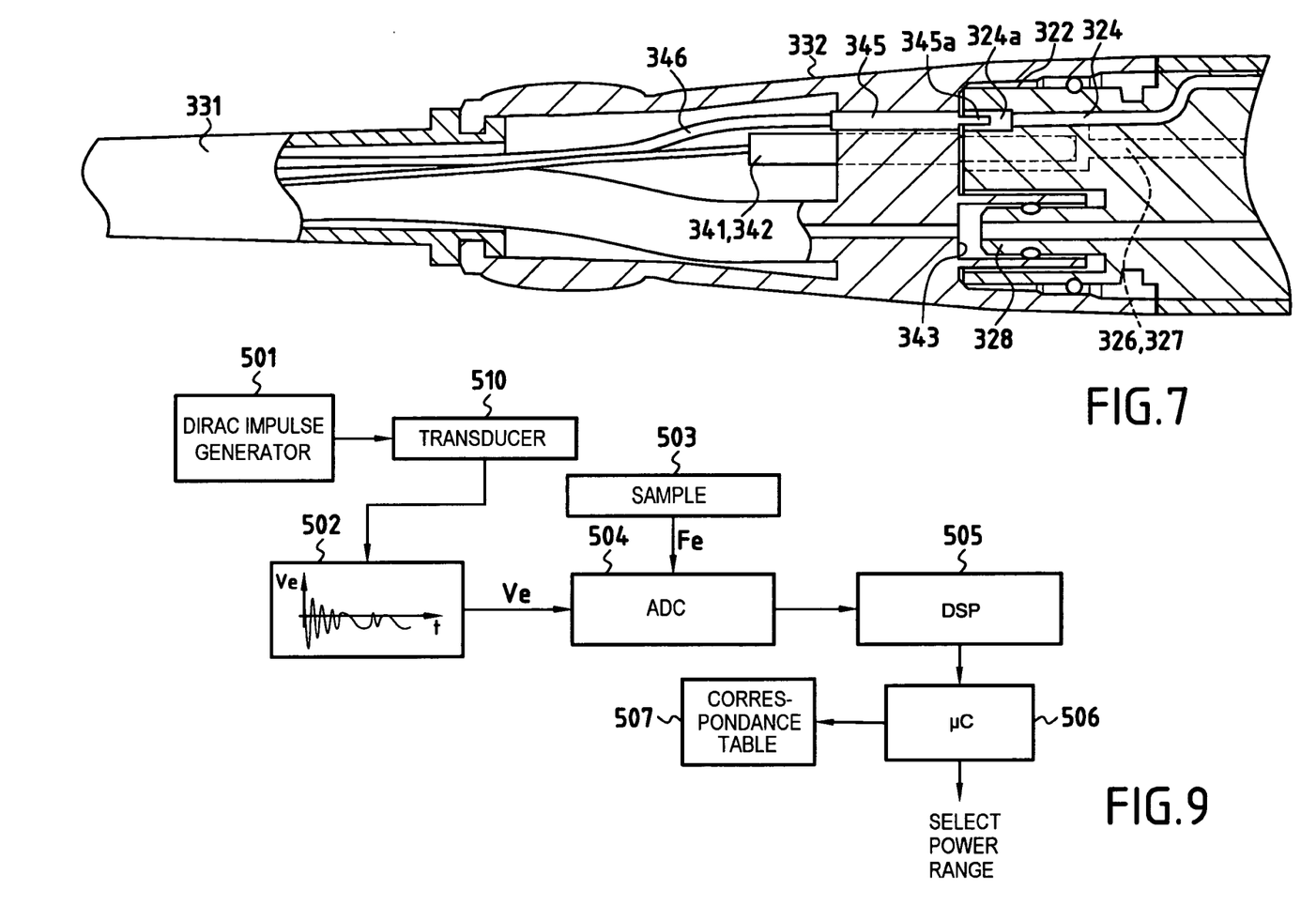
FIG. 7 is a longitudinal section view of a cord connector portion of the handpiece of the ultrasound generator of the FIG. 6 appliance.
FIG. 9 is a block diagram of a fourth embodiment of an ultrasound dental treatment appliance in accordance with the invention.

As shown in FIG. 7, the end 324a of the solenoid antenna 324 opens out into the bottom of the connector 322 of the handpiece 320 in the vicinity of the female sockets 326, 327 for powering the transducer and an irrigation duct 328 respectively co-operating with two male plugs 341 and 342 and a duct 343, all of these elements being placed inside a connector 332 connected to one end of the cord 331 and in which the connector 322 of the handpiece engages. The end 324a of the solenoid antenna forms, for example, a female socket into which a male plug 345a formed at the end of the conductor 346 is engaged. The end of the conductor 346 may also comprise a portion 345 including the capacitance of the LC transmitter circuit together with a power transistor (not shown). Putting these components in the connector 332 of the cord 331 makes it possible to limit losses and disturbances therein. The circuit formed in this way plays two roles: it powers the transponder 312 of the tip and it detects the encoded signal transmitted in response. In a variant embodiment, the solenoid antenna can be disposed outside the removable handpiece, e.g. in the connector 332 of the cord 331 by adapting the shape of the antenna and the frequency of the electromagnetic field generated.

Figure 8:
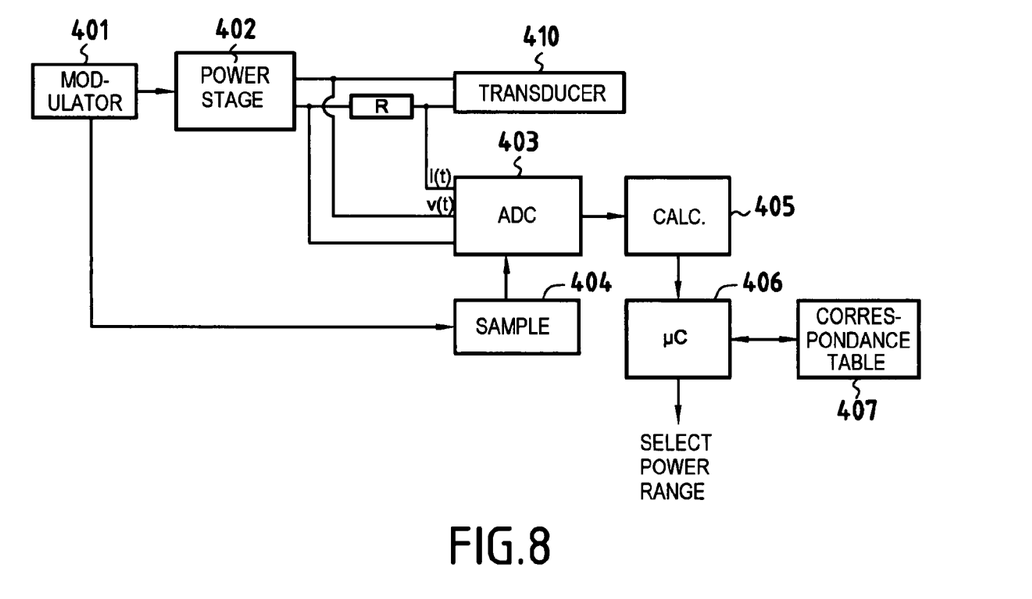
FIG. 8 is a block diagram of a third embodiment of an ultrasound dental treatment appliance in accordance with the invention.

With reference to FIG. 8 there follows a description of a third embodiment of the ultrasound appliance which, in accordance with the invention, enables the type of tip mounted on the handpiece to be recognized automatically and enables the corresponding power range to be selected automatically for the ultrasound generator. In this embodiment, the type of tip is recognized by frequency analysis of an electronic signal supplied to the transducer 410 of the handpiece. For this purpose, a frequency wobulator 401 is used that generates a signal around the resonant frequency of the assembly constituted by the transducer and the tip mounted on the handpiece. The current i(t) and the voltage v(t) at the terminals of the transducer are measured and converted into a digital signal by an analog-to-digital converter circuit 403. The digital signal is then forwarded to a calculator circuit 405 that serves to find the resonant frequencies of the transducer (its modes), its phase, its power, and its impedance. This information is used by the processor means 406 to determine the type of the tip, e.g. using a correspondence table 407 having recorded therein the types of tip in correspondence with said information, together with power and amplitude ranges for each of the types of tip in the list. All of the elements needed for this frequency analysis can be contained in the ultrasound generator, i.e. away from the separable handpiece.

In a fourth embodiment shown diagrammatically in FIG. 9, the type of tip mounted on the handpiece is recognized automatically and the corresponding power range is selected automatically by performing analysis in the time domain. Under such circumstances, a Dirac impulse generator 501 is used to analyze the response of the transducer 510 to a Dirac impulse using a digital signal processor (DSP) 505. The response signal 502 from the transducer is measured and then sampled by means of an analog-to-digital converter circuit 504 associated with a sampler 503. The digital values are stored in memory. The digital signal processor 505 processes these values digitally in order to extract pertinent signal information, i.e. the time signal of the tip. This signal is then forwarded to processor means 506 programmed to determine the type of tip that corresponds to the measured signal, e.g. by using a correspondence table enabling types of tip to be determined as a function of their time signatures. The correspondence table also contains the values for the power and amplitude ranges to be used in association with each type of tip, thus enabling the processor means 506 to control the ultrasound generator so as to set it on the power range that matches the tip.

The frequency domain and time domain analyses as performed respectively in the third and fourth above-described embodiments may optionally be implemented one after the other in a single ultrasound appliance. This makes it possible to obtain additional information about the tip mounted on the handpiece and to increase the precision with which a tip is recognized automatically.

Whatever the mode used for detecting the tip (bar code, RFID, frequency- and time-domain analyses), the processor means automatically set the ultrasound generator to a determined power and amplitude range that is adapted to using the tip. It is known that a single tip may be operated using different power and amplitude values as a function of the treatment that is to be applied (for example a single tip may be used both for removing scale and for debridement) or as a function of the case that is to be treated (e.g. as a function of the nature and/or the quantity of the material to be removed). In accordance with the invention, the practitioner can control the generator (e.g. using selection keys on the generator) to apply varying power and amplitude values to the tip, but can do only within the range that is selected automatically once the tip has been recognized. In this way, the practitioner is certain throughout the treatment always to apply power and amplitude values that are sufficient to enable the tip to operate effectively (above the bottom end of the range) and that are never too high given the strength specific to the tip (below the top limit of the range).

The solutions used in the third and fourth embodiments of the ultrasound appliance of the invention present an additional advantage compared with the first and second embodiments in that they do not require any modification of the tip (i.e. no bar code or transponder). All of the means needed for analysis purposes (whether in the frequency domain or the time domain) are included in the ultrasound generator, thus making it possible to detect conventional tips, given that their (frequency or time) response is specific to their structure.

The invention claimed is:

1. An ultrasound dental treatment appliance configured to receive ultrasound tips, the ultrasound dental treatment appliance comprising:
    a surgical handpiece fitted with a transducer connected to an ultrasound generator, said handpiece being configured to removably receive, one at a time, an ultrasound scaling tip, an ultrasound surfacing tip, and an ultrasound cutting tip, wherein the handpiece is configured such that the ultrasound tips are mechanically coupled to the transducer when received by the handpiece and operate in distinct different ultrasound power and amplitude ranges corresponding to the respective ultrasound tip type, information on the respective ultrasound tip types and corresponding ultrasound power and amplitude ranges being stored in a correspondence table;
    means for sending an impulse signal to the transducer;
    a digital signal processor that receives and extracts information from the transducer in the time domain; and
    a processor that uses the information extracted by the digital signal processor to determine the type of tip mounted on the handpiece and interrogates the correspondence table and adjusts the ultrasound generator to a power and amplitude range matching the determined type of tip, said range extending between a lower limit and an upper limit defining respective minimum and maximum power and amplitude values of the determined tip.

2. The appliance recited in claim 1, wherein the means for sending the impulse signal comprises a Dirac impulse generator.

3. A dental treatment appliance comprising:
    an ultrasound generator;
    a surgical handpiece comprising:
    a transducer connected to the ultrasound generator and configured to produce an ultrasound vibration based on input from the ultrasound generator; and
    an element mechanically coupled to the transducer, the element being configured to removably receive an ultrasound tip;
    means for sending an impulse signal to the transducer when an ultrasound tip is received on the element;
    a digital signal processor configured to receive and extract information from the transducer in the time; and
    a processor configured to:
    determine a type of ultrasound tip from the information extracted by the digital signal processor and interrogate a correspondence table to determine an ultrasound power and amplitude range corresponding to the type of ultrasound tip, the correspondence table including information on ultrasound power and amplitude ranges corresponding to each of a plurality of types of ultrasound tips; and
    adjust the ultrasound generator to cause the transducer to produce an ultrasound vibration within the power and amplitude range determined from the correspondence table.

4. The dental treatment appliance recited in claim 3, wherein the means for sending the impulse signal comprises a Dirac impulse generator.

5. The dental treatment appliance recited in claim 3, further comprising an ultrasound tip removably secured to the element so as to be mechanically coupled to the transducer, the response signal corresponding to the type of ultrasound tip removably secured to the element.

6. The dental treatment appliance recited in claim 5, wherein the type of ultrasound tip is one of: a scaling tip, a surfacing tip, and a cutting tip.

7. A dental treatment kit, comprising:
the dental treatment appliance as recited in claim 3; and
a plurality of ultrasound tips, each being removably securable to the element so as to be mechanically coupled to the transducer, each ultrasound tip corresponding to a different one of the types of ultrasound tips for which information is included in the correspondence table.

8. The dental treatment kit recited in claim 7, wherein the plurality of ultrasound tips comprises: a scaling tip, a surfacing tip, and a cutting tip.

* * * * *